(12) United States Patent
Midorikawa et al.

(10) Patent No.: US 10,342,988 B2
(45) Date of Patent: Jul. 9, 2019

(54) MAGNETIC STIMULATION DEVICE

(71) Applicant: TEIJIN PHARMA LIMITED, Tokyo (JP)

(72) Inventors: Masamichi Midorikawa, Hino (JP); Takamitsu Okayama, Hino (JP); Rei Tamiya, Hino (JP)

(73) Assignee: Teijin Pharma Limited, Tokyo (JP)

( * ) Notice: Subject to any disclaimer, the term of this patent is extended or adjusted under 35 U.S.C. 154(b) by 226 days.

(21) Appl. No.: 14/781,740

(22) PCT Filed: Mar. 28, 2014

(86) PCT No.: PCT/JP2014/059343
§ 371 (c)(1),
(2) Date: Oct. 1, 2015

(87) PCT Pub. No.: WO2014/163020
PCT Pub. Date: Oct. 9, 2014

(65) Prior Publication Data
US 2016/0030763 A1      Feb. 4, 2016

(30) Foreign Application Priority Data

Apr. 2, 2013   (JP) ................................. 2013-077155

(51) Int. Cl.
*A61N 2/02* (2006.01)
*A61N 2/00* (2006.01)

(52) U.S. Cl.
CPC .............. *A61N 2/02* (2013.01); *A61N 2/004* (2013.01); *A61N 2/006* (2013.01)

(58) Field of Classification Search
CPC ........... A61N 2/02; A61N 2/006; A61N 2/004
(Continued)

(56) References Cited

U.S. PATENT DOCUMENTS 5,984,854 A * 11/1999 Ishikawa .................. A61N 2/02
600/9
2009/0187062 A1   7/2009 Saitoh
(Continued)

FOREIGN PATENT DOCUMENTS

EP         2666515 A1    11/2013
JP      2008-543416 A    12/2008
(Continued)

OTHER PUBLICATIONS

International Search Report for PCT/JP2014/059343 dated May 27, 2014.
(Continued)

*Primary Examiner* — Kaylee R Wilson
(74) *Attorney, Agent, or Firm* — Sughrue Mion, PLLC

(57) ABSTRACT

Provided is a magnetic stimulation device, which does not feel hot to the user. The magnetic stimulation device (1) comprises: a contact plate (2) to be disposed near the user's head; an exciting coil (3) to be held above the contact plate (2); a casing (4), which covers at least the upper side of the exciting coil (3), in which openings (17, 18) are provided above the center of the exciting coil (3) winding, and in which a gap that is open on the outside of the exciting coil (3) is formed between the casing and the contact plate (2); and a suction fan (5) for drawing out air between the contact plate (2) and the casing (4) from the openings (17, 18) of the casing (4).

10 Claims, 8 Drawing Sheets

(58) Field of Classification Search
USPC .......................................................... 600/13
See application file for complete search history.

(56) References Cited

U.S. PATENT DOCUMENTS

2011/0021863 A1    1/2011   Burnett et al.
2012/0157752 A1    6/2012   Nishikawa et al.

FOREIGN PATENT DOCUMENTS

| JP | 2010-162204 A | 7/2010 |
| JP | 2013-500081 A | 1/2013 |
| WO | 2006/134598 A2 | 12/2006 |
| WO | 2007/123147 A1 | 11/2007 |
| WO | 2007/137887 A1 | 12/2007 |
| WO | 2011/011749 A1 | 1/2011 |
| WO | 2012/059917 A1 | 5/2012 |

OTHER PUBLICATIONS

International Preliminary Report on Patentability dated Oct. 15, 2015, for International Application No. PCT/JP2014/059343 filed Mar. 28, 2014, 6 pages.
Communication dated Mar. 3, 2016 from the European Patent Office in counterpart application No. 14778766.7.

* cited by examiner

MAGNETIC STIMULATION DEVICE

CROSS REFERENCE TO RELATED APPLICATIONS

This application is a National Stage of International Application No. PCT/JP2014/059343 filed Mar. 28, 2014 (claiming priority based on Japanese Patent Application No. 2013-077155 filed Apr. 2, 2013), the contents of which are incorporated herein by reference in their entirety.

TECHNICAL FIELD

The present invention relates to a magnetic stimulation device.

BACKGROUND ART

Non-invasive methods of treatment of, for example, intractable disease such as nerve damage include repetitive transcranial magnetic stimulation (rTMS). The repetitive transcranial magnetic stimulation is a method of treatment in which a symptom is ameliorated by giving a magnetic stimulation to a certain site (motor area) of the brain from the outside with a magnetic field generated by applying an electric current to a conductive coil brought closer to the head of a patient.

The repetitive transcranial magnetic stimulation requires the magnetic field allowed to act on the motor area of the brain corresponding to a disease. The coil is desirably disposed in as close contact as possible with the patient in terms of energy efficiency. For example, Patent Document 1 describes that a magnetic stimulation device used in the repetitive transcranial magnetic stimulation has a coil fixed to a shell like a cap or a helmet put on the head of a patient.

Because the coil generates heat due to energization and the magnetic stimulation device becomes hot when the device is continuously used, a patient may feel heat. Also, a patient may feel uncomfortably hot due to air heated by heat generation of the magnetic stimulation device and the patient may avoid the treatment.

To solve these problems, Patent Document 2 describes a method of cooling a coil by sending an air current in a direction so that the air current is not directly applied to a patient in a magnetic stimulation device for treatment of urinary incontinence having a magnetic stimulation unit disposed in a seating part.

Patent Document 3 describes a position setting method and a cooling mode in a transcranial magnetic stimulation system including a helmet. This document describes several techniques with respect to how to release heat generated from a magnetic coil giving stimulation to a treatment part mostly on the head. Specifically, the techniques include a cooling mode utilizing the heat of vaporization of Freon gas, a water-cooling mode utilizing water stored in a separate unit, and an air-cooling mode utilizing air. Among these, the water-cooling and air-cooling modes are described as bringing a radiator system into contact with a coil to stabilize the temperature of the coil. However, the cooling mode using Freon gas is not appropriate from the viewpoint of environment pollution. The water-cooling mode may lead to a considerably large-scale device because of use of a tank. Moreover, the water-cooling and air-cooling modes using the radiator system lead to an increase in size of a coil unit and generate a pressure loss and noise in the radiator, and it is not practical to use an device having such problems near the head (near the ears) of a patient. As the device is used for a longer time, the radiator may deteriorate and cause liquid leakage and, therefore, the device has a safety problem in terms of using the device near the top of the head of a patient for a long period.

Patent Document 4 discloses a cooling technique in which a coil and a fan are arranged inside a housing including a patient interface plate in this order from the interface plate so that air sucked from an inlet in a housing rear portion separate from a patient is brought into contact with the interface plate and the coil in series based on the drive of the fan. However, since the inlet is formed in the vicinity of the outer circumference of the housing (on the outside of the fan) in this cooling technique, the air sucked into the housing first cools a housing circumferential wall surrounding the circumference of the coil, then cools the interface plate, and finally cools the coil before being discharged from a center portion of the housing. Thus, when reaching the interface plate, the air is already warmed and, therefore, this cooling technique cannot achieve the original purpose of cooling the interface plate brought closest to the patient. Additionally, since a portion of the air sucked into the housing may immediately be discharged outside by the fan without cooling the interface plate or without cooling the coil, this cooling technique has a problem of inability to achieve sufficient cooling efficiency.

PRIOR ART DOCUMENT

Patent Documents

Patent Document 1: WO 2007/123147
Patent Document 2: JP 2010-162204 A
Patent Document 3: JP 2008-543416 A
Patent Document 4: JP 2013-500081 A

SUMMARY OF THE INVENTION

Problem to be Solved by the Invention

In view of the above, the present invention is to provide a magnetic stimulation device minimizing heat transmitted to a user such as a patient.

Means for Solving Problem

To solve the problem, a magnetic stimulation device according to the present invention has
a contact plate disposed near a head of a user;
an exciting coil held on the contact plate;
a casing covering at least an upper side of the exciting coil, the casing having an opening disposed above the exciting coil and a gap opened outside the exciting coil and formed between the casing and the contact plate; and
a suction fan for sucking air between the contact plate and the casing from the opening of the casing.

According to this arrangement, the air is sucked from the gap between the contact plate and the casing outside the exciting coil and forms an air flow between the contact plate and the exciting coil and the air is released above the user. As a result, the contact plate in contact with the user is cooled by the air and therefore is not excessively heated. The air heated by the contact with the exciting coil is exhausted above the user, preventing user from being exposed to hot air and also preventing him or her from feeling uncomfortable.

In another magnetic stimulation device of the present invention, the exciting coil is formed by winding a conductor in a planar manner, and the opening is positioned above a winding center of the exciting coil.

According to this arrangement, a space at the center of the exciting coil is used as an air flow passage and, therefore, a sufficient air flow rate can be ensured. Moreover, a uniform air flow can be formed so that the contact plate and the exciting coil are cooled evenly.

In another magnetic stimulation device of the present invention, the casing has a bottom surface portion covering the underside of the exciting coil to form an air flow passage between the bottom surface portion and the contact plate.

According to this arrangement, all the sucked air flows on the surface of the contact plate, effectively cooling the contact plate held on the user's head.

In another magnetic stimulation device of the present invention, the contact plate is a shell to be placed on the head of the user.

According to this arrangement, the magnetic stimulation device can readily be positioned. Also, the device can also be applied to home therapies.

Effect of the Invention

As described above, according to the present invention, the heat generated by the exciting coil is released above a patient by the suction fan to prevent the contact plate from being heated and, therefore, a user does not feel uncomfortably hot.

DESCRIPTION OF THE EMBODIMENTS

Figure 1:
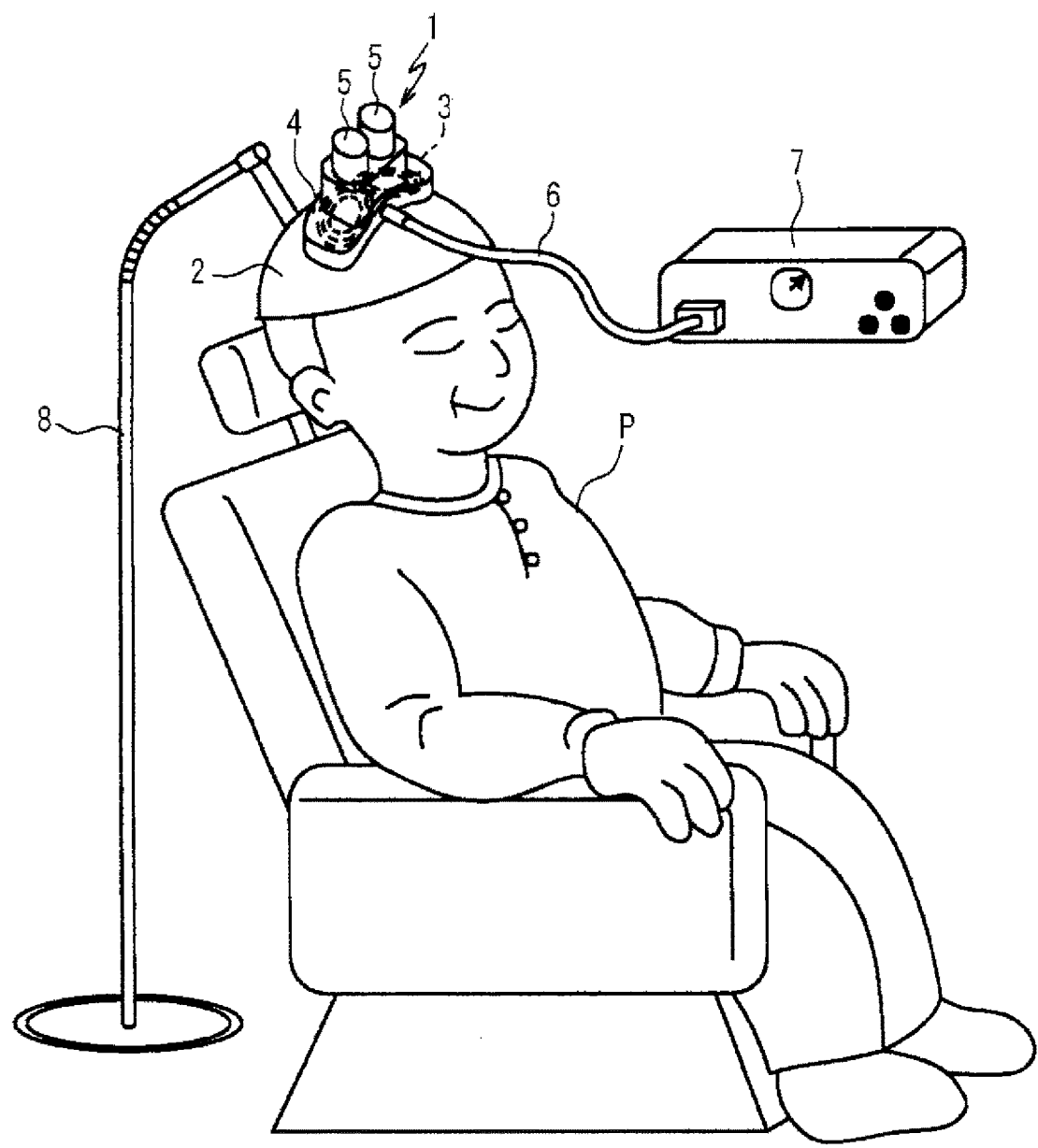
FIG. 1 is a schematic perspective view of a magnetic stimulation device in use of a first embodiment of the present invention.

An embodiment of the present invention will now be described with reference to the drawings. First, FIG. 1 schematically depicts a magnetic stimulation device 1 in use of a first embodiment of the present invention. The magnetic stimulation device 1 is used for repetitive transcranial magnetic stimulation (rTMS) that is a method of treatment of nerve damage, for example. The magnetic stimulation device 1 has a hard shell (cap) 2 that is an example of a contact plate applied to a user P and that is formed to be in as close contact as possible with the head of the user P when being put on the head of the user P, a casing 4 attached to the shell 2 to house therein an exciting coil 3 wound in the form of figure-of-eight, and two suction fans 5 arranged on an upper portion of the casing 4.

The exciting coil 3 is configured so that it is supplied with electric power via a cable 6 from a drive device 7. This allows the exciting coil 3 to form a magnetic field to apply a magnetic stimulation to a site of the brain associated with the disease of the user P. To assist accurate positioning of the exciting coil 3 at a desired part of the user P, the shell 2 is supported by a supporting member 8.

Figure 2:
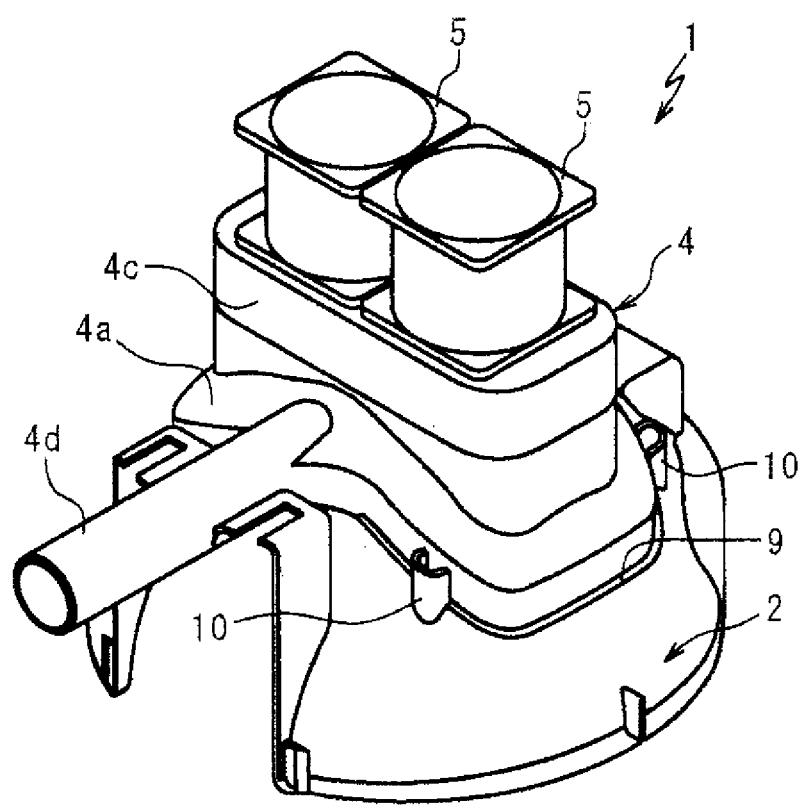
FIG. 2 is an enlarged perspective view of the magnetic stimulation device of FIG. 1.
Figure 3:
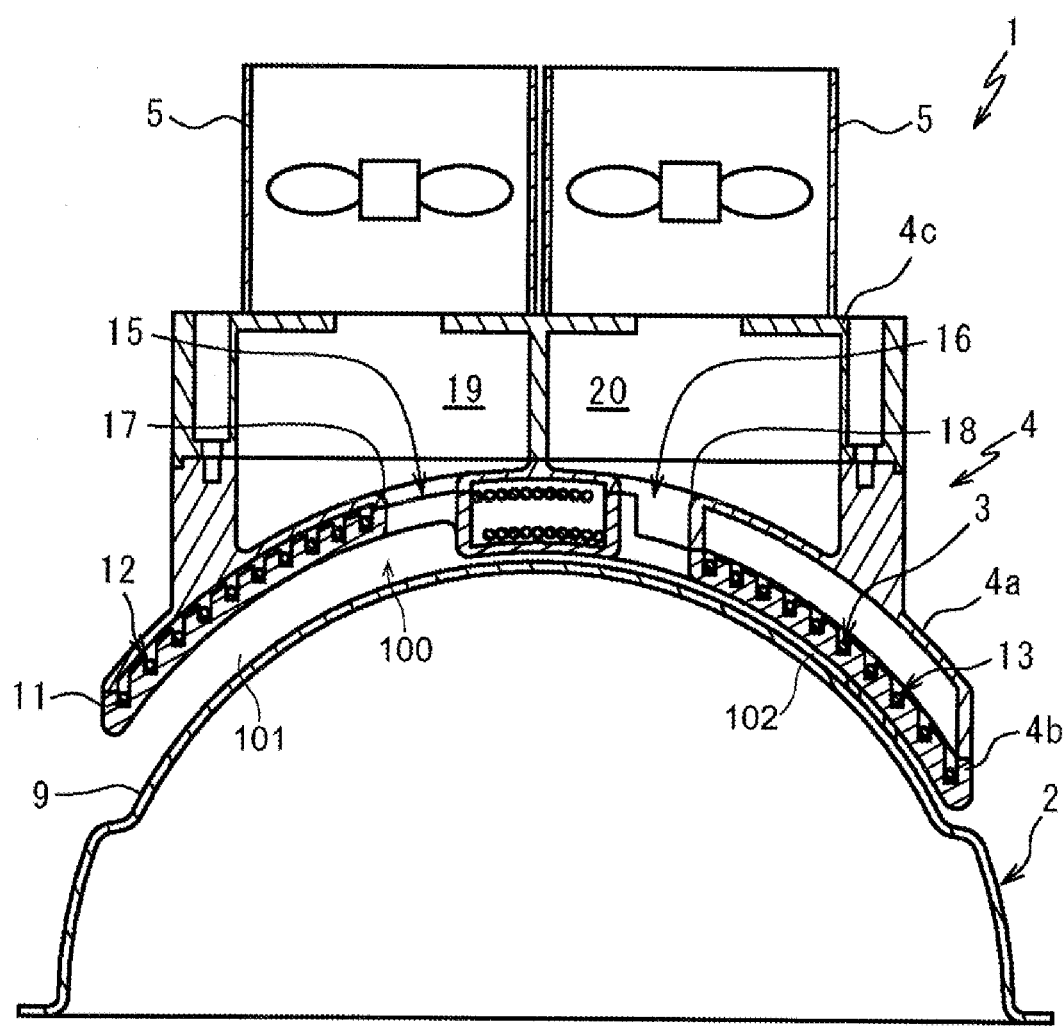
FIG. 3 is a cross-sectional view of a casing of the magnetic stimulation device of FIG. 2.

FIGS. 2 and 3 depict a detailed structure of the magnetic stimulation device 1. The shell 2 is provided with a recess 9 corresponding to the casing 4, and a holding protrusion 10 positioning and holding the casing 4. The holding protrusion 10 holds the casing 4 slightly apart from the shell 2 so as to leave a gap 100 is formed between the casing 4 and the shell 2. The gap 100 between the casing 4 and the shell 2 is preferably about 1 to 3 mm.

Figure 9:
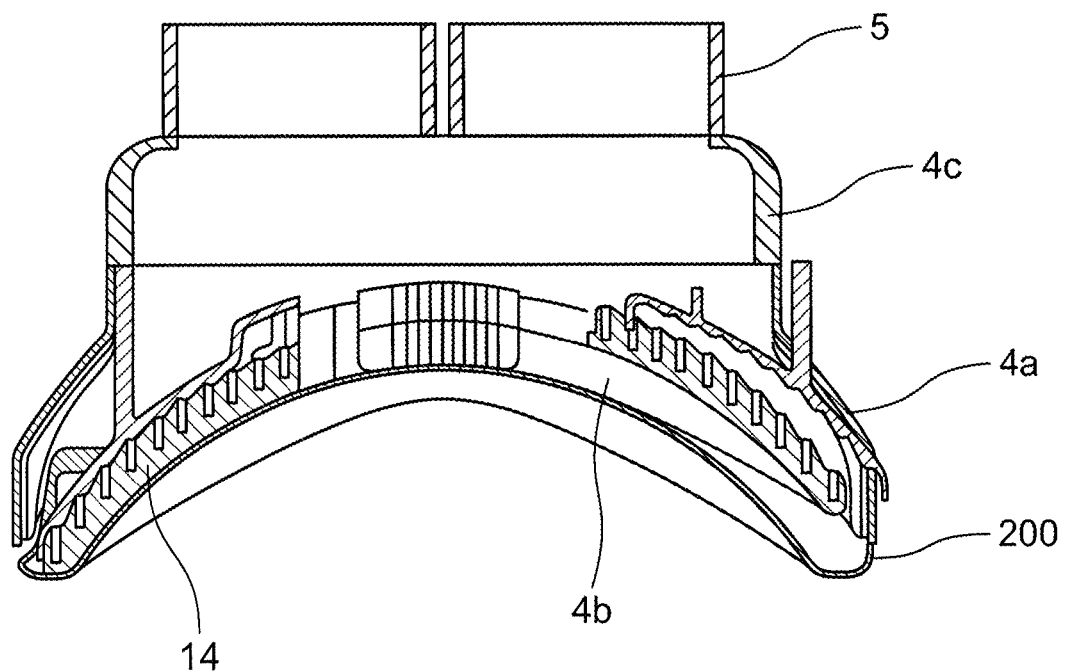
FIG. 9 is a cross-sectional view of a magnetic stimulation device of another embodiment of the present invention.

Although the shell 2 of FIG. 2 is formed into a helmet shape, the shape of the shell is not limited to the depicted helmet shape as long as a space can be formed between the casing 4 and the user's head. The shell 2 is configured so that the gap is ensured between the shell 2 and the casing 4 to prevent a bottom surface of the casing 4 from making a direct contact with the user. For example, as depicted in FIG. 9, a cover 200 may be disposed along a bottom surface of a main body portion 4a to cover the bottom surface. In this case, the cover 200 may be used instead of the shell. Also, the device can be handled with higher operability as compared to those having a helmet shape. The cover 200 may be formed of a member separated from the main body portion 4a and integrally assembled to the main body portion 4a or may integrally be formed as one member along with the main body portion 4a.

As depicted in a cross-sectional view of FIG. 3, the exciting coil 3 is made up of two loops 12, 13 each formed by winding a conductive wire 11 into an elliptic eccentric spiral shape that is planar (strictly speaking, curved to make up a portion of a spherical surface). The loops 12, 13 are held so that densely wound portions with narrow intervals between the neighborhood conductive wires 11 are overlapped with each other.

The casing 4 has the main body portion 4a covering the upper side of the exciting coil 3, a bottom surface portion 4b covering the underside of the exciting coil 3, a connecting portion 4c extending above the main body portion 4a to fix the suction fans 5, and a nozzle portion 4d for connecting a power cable not depicted. An inner surface of the bottom surface portion 4b is provided with a groove 14 receiving the conductive wire 11 for retaining the winding shape of the exciting coil 3 described above. The connecting portion 4c is a spacer separating the suction fans 5 from the exciting coil 3 to the extent that the intensity of the magnetic field formed by the exciting coil 3 is weakened with respect to the suction fans 5. Also in the form depicted in FIG. 9, the groove 14 holding the loops 12, 13 of the conductive wire 11 is formed in the main body portion 4a.

Figure 4:
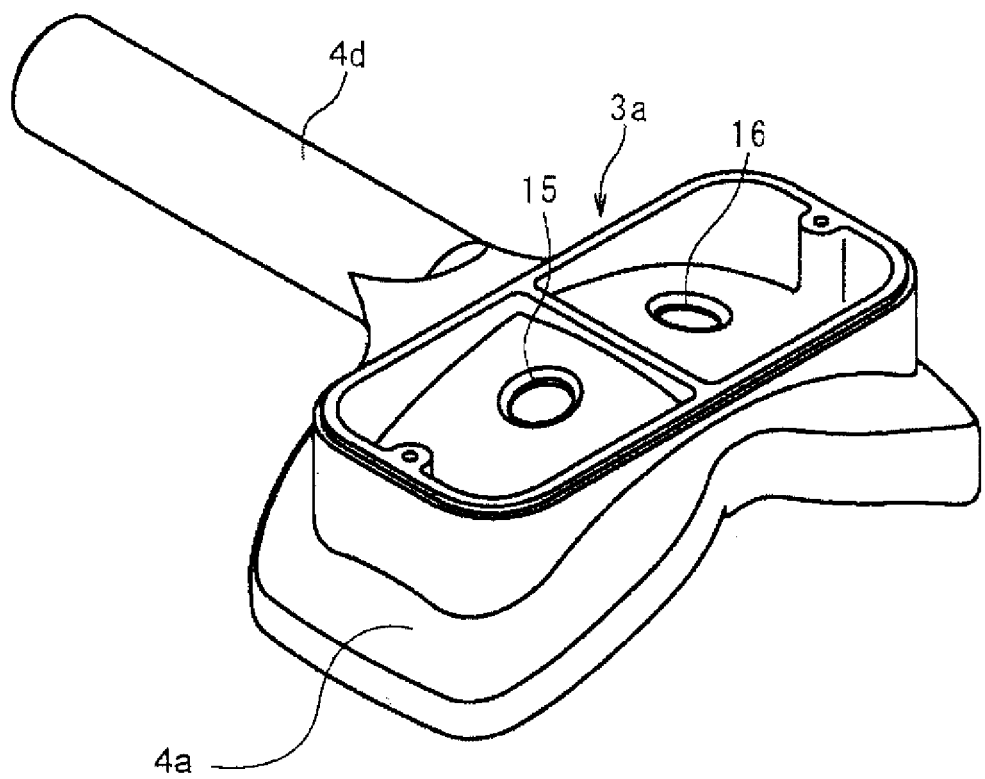
FIG. 4 is a perspective view of the casing of the magnetic stimulation device of FIG. 2.

The main body portion 4a and the bottom surface portion 4b of the casing 4 are provided with through-holes 15, 16 penetrating the winding centers of the loops 12, 13 of the exciting coil 3. These through-holes 15, 16 communicate with openings 17, 18 of the main body portion 4a formed above the centers of winding of the loops 12, 13 (see FIG. 4 mainly depicting the main body portion 4a of the casing 4). The inside of the connecting portion 4c is divided into two spaces 19, 20 respectively communicating with the through-holes 15, 16.

Figure 10:
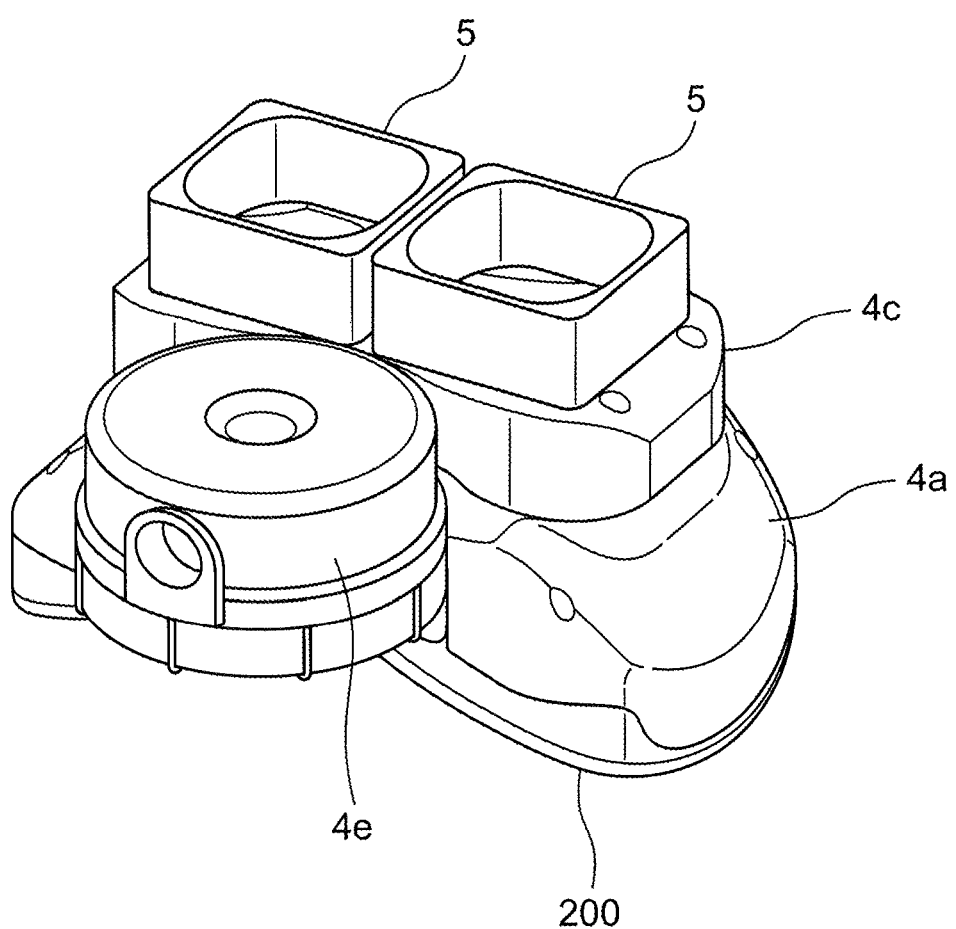
FIG. 10 is a perspective view of a magnetic stimulation device of another embodiment of the present invention.

The nozzle portion 4d is a passage of the power cable connected to the exciting coil and may have a cylindrical shape as depicted in FIG. 2 or may be a disk-shaped cable cap 4e rotatable clockwise and counterclockwise as depicted in FIG. 10. The form of the cable cap 4e as depicted in FIG. 10 increases a degree of freedom of cable route arrangement as compared to the form of the nozzle portion 4d depicted in FIG. 2. This prevents the cable from interfering with the supporting member or from bending as a result of the interference when the casing 4 is moved, regardless of the position or the direction of disposition of the coil. Therefore, a damage of the cable can be prevented and the magnetic stimulation device 1 can be reduced in size.

The suction fans 5 suck air around the casing 4 and the shell 2 through the through-holes 15, 16 from the gap opened outward on the outside of the exciting coil 3 between the shell 2 and the bottom surface portion 4b and discharge the air above the head of the user P. As a result, the heat generated by the exciting coil 3 is taken and dissipated into air above the user P. Since the air taken by the fans forms a dynamic heat-insulating layer between the shell 2 and the bottom surface portion 4b and this heat-insulating layer can directly or indirectly air-cool particularly the shell 2 in direct contact with the user P, as well as the exciting coil 3, the shell 2 is not heated to the extent that the user P feels heat even when the magnetic stimulation device 1 is continuously used. The hot air current used for the cooling is released above the user P and, therefore, the user P does not feel uncomfortably hot due to the hot air.

In this embodiment, an air current is caused to pass through the gap between the shell 2 and the bottom surface portion 4b by the suction air current of the suction fans 5 so as to form the heat-insulating layer between the shell 2 and the bottom surface portion 4b, thereby air-cooling the shell 2 that is a part contacting the user and the bottom surface portion 4b contacting a coil loop portion.

The coil cooling effect to the loops 12, 13 is acquired regardless of whether the gap between the shell 2 and the bottom surface portion 4b is uniform. Describing in terms of this embodiment, the reason is that no significant difference is made in an amount of air passing through the through-hole 15 and the through-hole 16 even if a size of the gap between the shell 2 and the bottom surface portion 4b in the portion corresponding to the loop 12 is different from a size of the gap between the shell 2 and the bottom surface portion 4b in the portion corresponding to the loop 13. Therefore, insufficient cooling is not caused by a reduction in air amount in a portion corresponding to either the loop 12 or the loop 13. To share the cooling efficiency of the loop 12 and the loop 13 between the respective suction fans 5, at least one of the shell 2 and the bottom surface portion 4b may be provided with a partition wall partitioning between a gap portion 101 corresponding to the loop 12 and a gap portion 102 corresponding to the loop 13.

To enhance the cooling effect to a coil portion, the gap portion 101 adjacent to the loop 12 between the shell 2 and the bottom surface portion 4b may be separated from the gap portion 102 adjacent to the loop 13 so that all or most of the air sucked by one of the suction fans 5 is applied to the gap portion 101 adjacent to the loop 12 to mainly cool the loop 12 while all or most of the air sucked by the other of the suction fans 5 is applied to the gap portion 102 adjacent to the loop 13 to mainly cool the loop 13.

A hole (not depicted) penetrating the bottom surface portion 4b and communicating with the conductive wire housing groove 14 can be formed in the main body portion 4a to bring a portion of the air flowing through the gap between the bottom surface portion 4b and the shell 2 into contact with the conductive wire 11 housed in the housing groove 14 so as to directly cool the conductive wire 11.

A connecting portion between the coil and the power cable may have the structure of the nozzle 4d depicted in FIG. 2 or may have the structure of the coil cap 4e depicted in FIG. 10.

Figure 5:
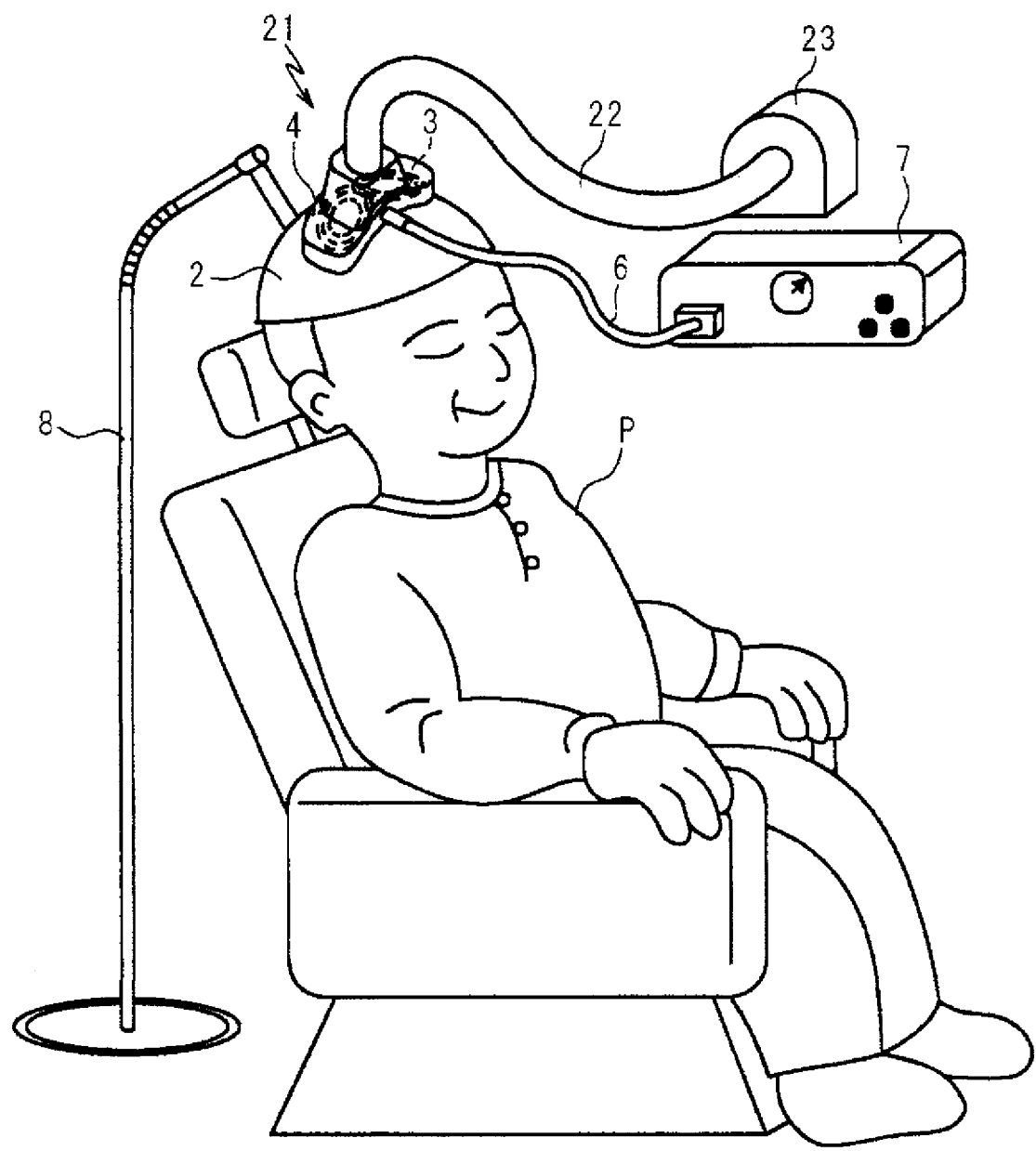
FIG. 5 is a schematic perspective view of a magnetic stimulation device in use of a second embodiment of the present invention.

FIG. 5 depicts a schematic of a magnetic stimulation device 21 of a second embodiment of the present invention. In this embodiment, the same structural elements as those of the first embodiment are denoted by the same reference numerals and will not redundantly be described.

The magnetic stimulation device 21 of this embodiment is connected through one flexible hose 22 on the casing 4 to one suction fan 23 disposed outside. Therefore, the connecting portion 4c of the casing 4 has a shape adaptable to connection with the flexible hose 22. Since the only one suction fan 23 is used in the magnetic stimulation device 21, the casing 4 is preferably disposed with an orifice or a damper for enabling adjustment of distribution of air flow volume between the portion corresponding to the loop 12 and the portion corresponding to the loop 13. Of course, the two flexible hoses 22 may be used for separately sucking air.

Figure 6:
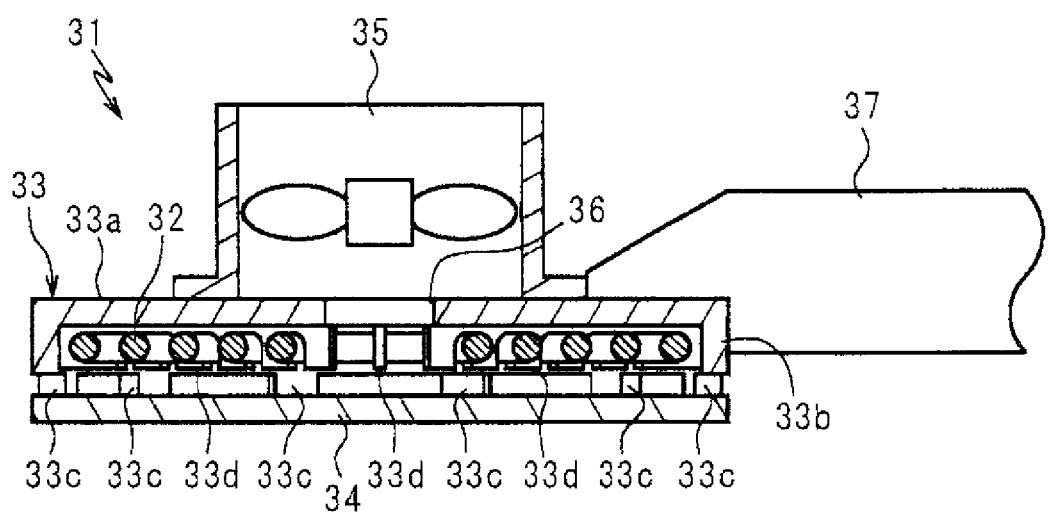
FIG. 6 is a schematic cross-sectional view of a magnetic stimulation device of a third embodiment of the present invention.

FIG. 6 depicts a schematic of a magnetic stimulation device 31 of a third embodiment of the present invention. In this embodiment, no structural element is placed on the head of a user and the device is held by, for example, a physician's hand or by using another supporting tool so that the device is located and used near the head of the user.

The magnetic stimulation device 31 has a casing 33 housing an exciting coil 32 and opened at its bottom, a contact plate 34 connected to the bottom opening of the casing 33, and a suction fan 35 attached to the upper side of the casing 33. The casing 33 has a main body portion 33a covering the upper side of the exciting coil 32, a peripheral wall portion 33b protruding downward from the outer circumference of the main body portion 33a and covering the outer circumference of the exciting coil 32, a plurality of connecting protrusions 33c disposed in a protruding manner on the lower end of the peripheral wall portion 33b at equal circumferential intervals to fix the contact plate 34, and a plate-shaped coil holding portion 33d disposed radially on an undersurface of the main body portion 33a. The coil holding portion 33d is provided with a plurality of cutouts each receiving a conductive wire making up the exciting coil 32. The main body portion 33a has an opening 36 formed in an upper portion of the winding center of the exciting coil 32 to allow the suction fan 35 to exhaust air. The magnetic stimulation device 31 also includes a grip 37 for gripping by a doctor's hand or some kind of a gripping tool. The grip 37 is also a passage for inserting a cable supplying power to the exciting coil 32.

In this embodiment, air is sucked from a gap between the peripheral wall portion 33b of the casing 33 and the contact plate 34 by a suction force of the suction fan 35. The sucked air not only flows along the contact plate 34 but also passes through gaps between the conductive wires of the exciting coil 32 and reaches the opening 36 via a space between the main body portion 33a of the casing 33 and the exciting coil 32. Therefore, the exciting coil 32 acting as a heat source is directly air-cooled in this embodiment.

Figure 7:
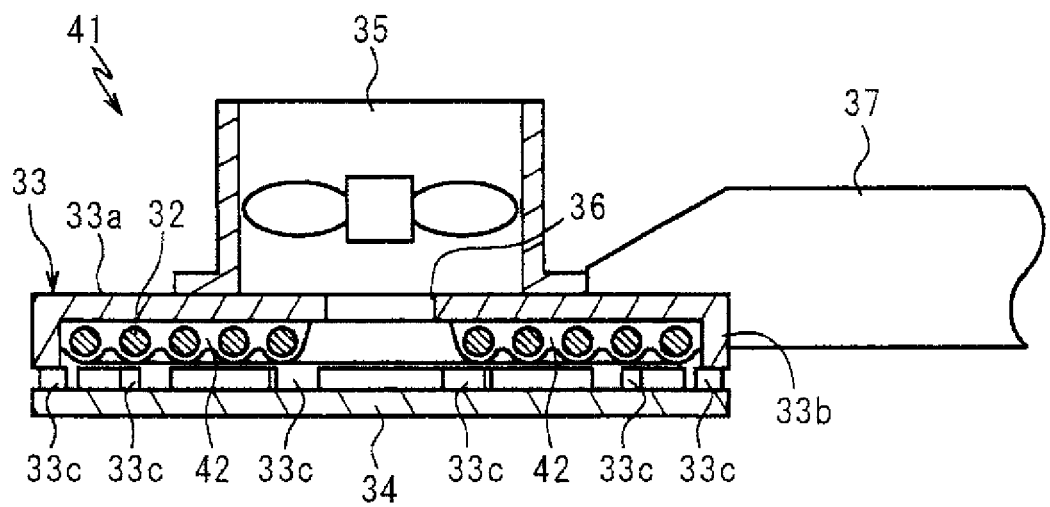
FIG. 7 is a schematic cross-sectional view of a magnetic stimulation device of a fourth embodiment of the present invention.

FIG. 7 depicts a magnetic stimulation device 41 of a fourth embodiment of the present invention. This embodiment is achieved by making a change in the magnetic stimulation device 31 of the third embodiment and, therefore, the same structural elements are denoted by the same reference numerals and will not redundantly be described. The magnetic stimulation device 41 has the exciting coil 32 fixed by, for example, an epoxy resin 42 applied and hardened onto the undersurface of the main body portion 33a of the casing 33, instead of the coil holding portion 33d of the magnetic stimulation device 31.

In this embodiment, the air sucked from the gap between the peripheral wall portion 33b of the casing 33 and the contact plate 34 flows only along the contact plate 34 without flowing between the conductive wires of the exciting coil 32 because of the presence of the epoxy resin 42 and is discharged through the opening. Although the contact plate 34 directly contacting a user is mainly cooled, this embodiment also provides the effect of cooling the exciting coil 32 via the epoxy resin 42.

Figure 8:
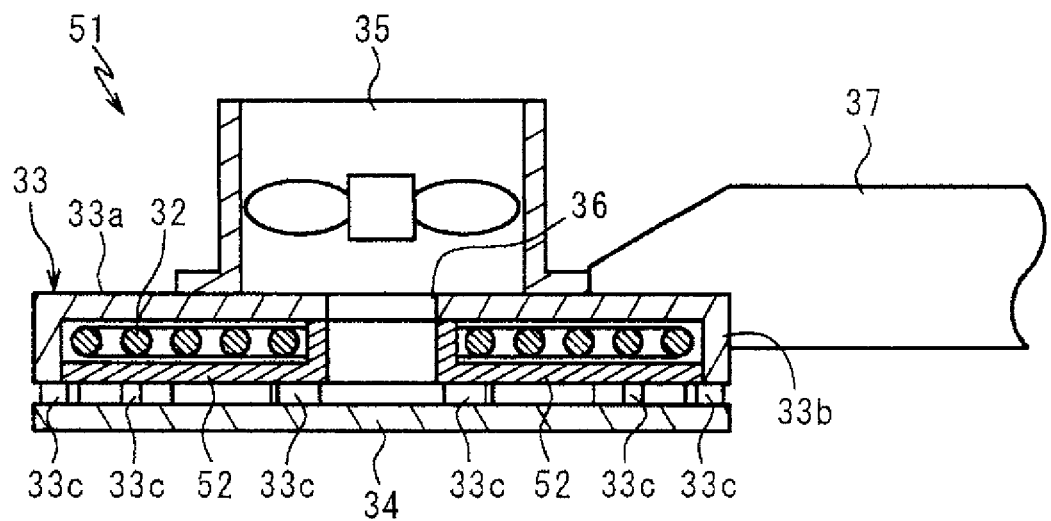
FIG. 8 is a schematic cross-sectional view of a magnetic stimulation device of a fifth embodiment of the present invention.

FIG. 8 depicts a magnetic stimulation device 51 of a fifth embodiment of the present invention. This embodiment is achieved by modifying the magnetic stimulation device 31 of the third embodiment and, therefore, the same structural elements are denoted by the same reference numerals and will not redundantly be described. The casing 33 of the magnetic stimulation device 51 includes a bottom surface portion 52 covering the inner circumference and the underside of the exciting coil 32, instead of the coil holding portion 33d of the magnetic stimulation device 31.

This embodiment has a simple structure and is readily assembled; however, it may require that the exciting coil 32 maintains its shape. Although the contact plate 34 can be cooled by air sucked by the suction fan 35, the exciting coil 32 cannot directly be cooled and, therefore, this embodiment is applied when the heat generation amount of the exciting coil 32 is not so large. To add an ability to cool the exciting coil 32, a small opening may be disposed in the bottom surface portion 52 of the casing 33 and, in some cases, also in the peripheral wall portion 33b, so that air is exhausted from the opening 36 through an internal space of the casing 33 housing the exciting coil 32.

Of course, even in the embodiments without the contact plate mounted on the user P such as the shell 2 of the first and second embodiments so that the device is intended to be positioned to the user by another means as in the third to fifth embodiments, the suction fan 35 may be disposed outside to suck air from an upper portion of the exciting coil 32 through a flexible hose etc.

PARTS LIST 1, 21, 31, 41, 51: magnetic stimulation device
2: shell (contact plate)
3, 32: exciting coil
4, 33: casing
4a, 33a: main body portion
4b, 52: bottom surface portion
4c: connecting portion
5, 23, 35: suction fan
11: conductive wire
12, 13: loop
15, 16: through-hole
17, 18, 36: opening
22: flexible hose
34: contact plate

The invention claimed is:

1. A transcranial magnetic stimulation device comprising:
a contact plate configured to be disposed near a head of a user;
an exciting coil held above the contact plate;
a casing disposed above the contact plate, the casing having upper and lower portions covering upper and lower portions of the exciting coil, respectively, and an opening extending through the upper and lower portions of the casing, the lower portion of the casing fully covering the lower portion of the exciting coil and defining a space between the lower portion of the casing and the contact plate, the space opening directly to an atmosphere outside the device and in direct communication with the opening; and
a fan, disposed above the opening, for directly drawing air from the atmosphere into the space and between the contact plate and the lower portion of the casing.

2. The transcranial magnetic stimulation device of claim 1,
wherein the exciting coil is formed by winding a conductor in a planar manner, and
wherein the opening is positioned above a winding center of the exciting coil.

3. The transcranial magnetic stimulation device of claim 1, wherein the contact plate is a shell configured to be placed on the head of the user.

4. The transcranial magnetic stimulation device in claim 1, wherein the contact plate has a same shape as a bottom surface of the lower portion of the casing and covers the bottom surface.

5. The transcranial magnetic stimulation device in claim 1, wherein the fan cools the exciting coil with air introduced into the space and forms a dynamic heat-insulating layer of the air introduced in the space to prevent a temperature increase of the contact plate.

6. A transcranial magnetic stimulation device comprising:
a contact plate configured to be disposed near a head of a user;
an exciting coil held above the contact plate;
a casing disposed above the contact plate, the casing having upper and lower portions covering upper and lower portions of the exciting coil, respectively, and an opening extending through the upper and lower portions of the casing, the lower portion of the casing fully covering the entire lower surface of the exciting coil and defining a space between the lower portion of the casing and the contact plate, the space opening directly to an atmosphere outside the device and in communication with the opening; and
a fan, disposed above the opening, for directly drawing air from the atmosphere into the space and between the contact plate and the lower portion of the casing.

7. The transcranial magnetic stimulation device of claim 6,
wherein the exciting coil is formed by winding a conductor in a planar manner, and
wherein the opening is positioned above a winding center of the exciting coil.

8. The transcranial magnetic stimulation device of claim 6, wherein the contact plate is a shell configured to be placed on the head of the user.

9. The transcranial magnetic stimulation device in claim 6, wherein the contact plate has a same shape as a bottom surface of the lower portion of the casing and covers the bottom surface.

10. The transcranial magnetic stimulation device in claim 6, wherein the fan cools the exciting coil with air introduced into the space and forms a dynamic heat-insulating layer of the air introduced in the space to prevent a temperature increase of the contact plate.

\* \* \* \* \*